US011337942B2

(12) United States Patent
Yoon et al.

(10) Patent No.: US 11,337,942 B2
(45) Date of Patent: May 24, 2022

(54) EXTERNAL USE COMPOSITION COMPRISING PAEONOL AND PANTHENOL OR PHARMACEUTICALLY ACCEPTABLE SALTS THEREOF AS ACTIVE INGREDIENTS

(71) Applicant: GENTRIBIO INC., Chuncheon-si (KR)

(72) Inventors: Chang Keun Yoon, Chuncheon-si (KR); Hong Gyum Kim, Chuncheon-si (KR)

(73) Assignee: GENTRIBIO INC., Chuncheon-si (KR)

( * ) Notice: Subject to any disclaimer, the term of this patent is extended or adjusted under 35 U.S.C. 154(b) by 0 days.

(21) Appl. No.: 17/644,299

(22) Filed: Dec. 14, 2021

(65) Prior Publication Data

US 2022/0117918 A1    Apr. 21, 2022

Related U.S. Application Data

(63) Continuation of application No. PCT/KR2020/017469, filed on Dec. 2, 2020.

(30) Foreign Application Priority Data

Dec. 16, 2019    (KR) .................. 10-2019-0167889

(51) Int. Cl.
*A61K 31/164* (2006.01)
*A61K 31/12* (2006.01)
(Continued)

(52) U.S. Cl.
CPC ............ *A61K 31/164* (2013.01); *A61K 31/12* (2013.01); *A61K 31/122* (2013.01);
(Continued)

(58) Field of Classification Search
CPC .... A61K 2800/782; A61K 8/63; A61Q 19/00; A61Q 19/008; A61Q 19/02; A61Q 19/08;
(Continued)

(56) References Cited

U.S. PATENT DOCUMENTS

| 4,602,036 A | 7/1986 | Hanck et al. |
| 2005/0136085 A1* | 6/2005 | Bellamy ................ A61Q 19/00 424/769 |

(Continued)

FOREIGN PATENT DOCUMENTS

| CN | 102552061 A | 7/2012 |
| CN | 106420605 A | 2/2017 |

(Continued)

OTHER PUBLICATIONS

Bylka et al., "*Centella asiatica* in cosmetology", Postępy Dermatologii i Alergologii XXX; Jan. 2013, pp. 46-49.

(Continued)

*Primary Examiner* — Savitha M Rao
(74) *Attorney, Agent, or Firm* — Knobbe Martens Olson & Bear LLP (57) ABSTRACT

Provided are a medical ointment of a novel combination containing paeonol and a pharmaceutical use thereof. The medical ointment of a novel combination includes paeonol and panthenol, and further includes at least one selected from *Centella asiatica*, coenzyme Q10, neomycin sulfate, and pharmaceutically acceptable salts of these. In the medical ointment of a novel combination, specific ingredients that are effective for local pain relief are mixed with ingredients having other effects in a certain ratio to address the problems of the cut treatment ointment of the related art, so that excellent effects may be obtained in relieving itching and reducing pain while inflammation is effectively treated.

3 Claims, 6 Drawing Sheets

(51) Int. Cl.
| | |
|---|---|
| *A61P 17/02* | (2006.01) |
| *A61K 36/23* | (2006.01) |
| *A61K 31/7036* | (2006.01) |
| *A61K 31/122* | (2006.01) |
| *A61P 17/04* | (2006.01) |

(52) U.S. Cl.
CPC .......... *A61K 31/7036* (2013.01); *A61K 36/23* (2013.01); *A61P 17/02* (2018.01); *A61P 17/04* (2018.01)

(58) Field of Classification Search
CPC .......... A61Q 19/10; A61Q 1/14; A61Q 5/006; A61Q 5/02
See application file for complete search history.

(56) References Cited

U.S. PATENT DOCUMENTS

| | | | |
|---|---|---|---|
| 2006/0110415 | A1 | 5/2006 | Gupta |
| 2009/0042846 | A1* | 2/2009 | Gupta .................... A61Q 19/00 540/58 |

FOREIGN PATENT DOCUMENTS

| | | | |
|---|---|---|---|
| KR | 10-2015-0000381 A | | 1/2015 |
| KR | 10-2015-0018259 A | | 2/2015 |
| KR | 10-2015-0087140 A | | 7/2015 |
| KR | 10-1732844 B1 | | 4/2017 |
| KR | 10-2018-0124424 A | | 11/2018 |
| KR | 10-1949270 B1 | | 2/2019 |
| KR | 10-2019-0090955 A | | 8/2019 |

OTHER PUBLICATIONS

Camargo et al., "Skin moisturizing effects of panthenol-based formulations", J. Cosmet. Sci., 62, 361-369 (Jul./Aug. 2011).
Choi et al., "Effect of coenzyme Q10 on cutaneous healing in skin-incised mice", Arch Pharm Res vol. 32, No. 6, 907-913, 2009, DOI 10.1007/s12272-009-1613-3.
Chou, "Anti-inflammatory and analgesic effects of paeonol in carrageenan-evoked thermal hyperalgesia", British Journal of Pharmacology (2003) 139, 1146-1152.
Ebner et al., "Topical use of dexpanthenol in skin disorders", Am J Clin Dermatol 2002; 3 (6): 427-433.
Fu et al., "Anti-inflammatory and anticoagulative effects of paeonol on LPS-induced acute lung injury in rats", Evidence-Based Complementary and Alternative Medicine, vol. 2012, Article ID 837513, 12 pages, doi:10.1155/2012/837513.
Jin et al., "Anti-inflammatory and anti-oxidative activities of paeonol and its metabolites through blocking MAPK/ERK/p38 signaling pathway", Inflammation, 2015, DOI: 10.1007/s10753-015-0265-3, 13 pages.
Liu et al., "Paeonol attenuated inflammatory response of endothelial cells via stimulating monocytes-derived exosomal microRNA-223", Frontiers in Pharmacology, Nov. 2018, 12 pages.
Liu et al., "Prevention of bleomycin-induced pulmonary inflammation and fibrosis in mice by paeonol", Frontiers in Physiology, Mar. 2017, 10 pages.
Meng et al., "Paeonol inhibits the development of 1-chloro-2,4-dinitrobenzene-induced atopic dermatitis via mast and T cells in BALB/c mice", Molecular Medicine Reports 19: 3217-3229, 2019.
Nam et al., Paeonol attenuates inflammation-mediated neurotoxicity and microglial activation, Traditional Chinese Medicine and Neural Regeneration, 8:18, 2013, pp. 1637-1643.
Proksch, "Topical use of dexpanthenol: a 70th anniversary article", Journal of Dermatological Treatment, 2017 DOI: 10.1080/09546634. 2017.1325310, 9 pages.
Schniertshauer et al., "Age-dependent loss of mitochondrial function in epithelial tissue can be reversed by coenzyme $Q_{10}$", Journal of Aging Research, vol. 2018, Article ID 6354680, 8 pages.
Stettler et al., "A new topical panthenol-containing emollient: Results from two randomized controlled studies assessing its skin moisturization and barrier restoration potential, and the effect on skin microflora", Journal of Dermatological Treatment, 2016 DOI: 10.1080/09546634.2016.1214235, 35 pages.
Xue et al., "Paeonol suppresses solar ultraviolet-induced skin inflammation by targeting T-LAK cell-originated protein kinase", Oncotarget, 2017, vol. 8, (No. 16), pp. 27093-27104.
Zong et al., "Beneficial anti-inflammatory effect of paeonol self-microemulsion-loaded colon-specific capsules on experimental ulcerative colitis rats", Artificial Cells, Nanomedicine, and Biotechnology, 2018, DOI: 10.1080/21691401.2017.1423497, 13 pages.
Notice of Allowance dated Nov. 11, 2021 in Korean Application No. 10-2020-0166560 which claims priority to Korean Application No. 10-2019-0167889.
International Search Report and Written Opinion dated Apr. 14, 2021 in PCT/KR2020/0174679.
Notice of Preliminary Examination Results dated Sep. 23, 2021 in Korean Patent Application No. 10-2020-0166560.

* cited by examiner

EXTERNAL USE COMPOSITION COMPRISING PAEONOL AND PANTHENOL OR PHARMACEUTICALLY ACCEPTABLE SALTS THEREOF AS ACTIVE INGREDIENTS

CROSS REFERENCE TO RELATED APPLICATIONS

This is a continuation of International Patent Application No. PCT/KR2020/017469, filed on Dec. 2, 2020, which claims priority to Korean Patent Application No. 10-2019-0167889 filed on Dec. 16, 2019, contents of both of which are incorporated herein by reference in their entireties.

BACKGROUND

Technical Field

The present disclosure relates to a medical ointment containing paeonol and panthenol and a pharmaceutical use thereof, and more particularly, to a medical ointment of a novel combination containing paeonol and panthenol and a pharmaceutical use thereof, the medical ointment exhibiting excellent effects in suppressing pruritus and pain while effectively treating inflammation, by solving the problems of wound treatment ointments of the related art.

Description of Related Technology

Inflammation is typically characterized by a localized tissue response to, for example, invasion of microorganisms, specific antigens, damaged cells, or physical or chemical factors, and an inflammatory response is a normally protective mechanism that not only initiates the treatment of tissues, but also destroy, dilute, or sequester both detrimental agents and damaged tissues. Such inflammation may arise from physical trauma, infection, some chronic diseases (for example, autoimmune diseases such as psoriasis and rheumatoid arthritis) or chemical or physiological responses to external stimuli (for example, part of an allergic reaction). Inflammatory mediators can increase blood flow and dilation of local blood vessels, resulting in redness and heat, effusion of body fluids, often causing local edema, migration of white blood cells to the inflammatory site, and pain, and many diseases are characterized by abnormal tissue damage inflammation and caused thereby. These conditions are typically characterized by the activation of immune defense mechanisms, which can result in more detrimental than beneficial effects on the host, and are generally associated with varying degrees of tissue redness or hyperemia, swelling, high fever, pain, itching, cell death, tissue destruction, cell proliferation, or loss of function, and examples thereof include inflammatory bowel disease, rheumatoid arthritis, multiple sclerosis, psoriasis, glomerulonephritis, and transplant rejection. These inflammatory changes are triggered by a series of cellular and biochemical events involving cells such as neutrophils, monocytes, macrophages, and lymphocytes, along with inflammatory mediators such as vasoactive amines, cytokines, complement factors, and reactive oxygen species, and, most of all, inflammation plays an important role in the wound healing process. Thus, wounds such as cuts, and burns can be classified as conditions associated with inflammation. It is generally considered in the art that anti-inflammatory drugs should not act directly on open wounds since they may be detrimental to the progress of wound healing.

In consideration of the above points, conventionally developed and provided ointments for the treatment of wounds, such as cuts, or burns include Fucidin™, Composite Madecassol™ and Madecassol Care™.

NON-PATENT DOCUMENTS (Non-Patent Document 1) Non-Patent Document 1: Br J Pharmacol 2003 July; 139(6):1146-52 Anti-inflammatory and analgesic effects of paeonol in carrageenan-evoked thermal hyperalgesia (Non-Patent Document 2) Non-Patent Document 2: Artificial Cells, Nanomedicine, and Biotechnology: An International Journal Volume 46, 2018—Issue sup1: Supplement 1 Beneficial anti-inflammatory effect of paeonol self-microemulsion-loaded colon-specific capsules on experimental ulcerative colitis rats (Non-Patent Document 3) Non-Patent Document 3: Evidence-Based Complementary and Alternative Medicine Volume 2012, Article ID837513, 12 pages Anti-Inflammatory and Anticoagulative Effects of Paeonol on LPS-Induced Acute Lung Injury in Rats (Non-Patent Document 4) Non-Patent Document 4: Front Pharmacol, 20 Nov. 2018 Paeonol Attenuated Inflammatory Response of Endothelial Cells via Stimulating Monocytes-Derived Exosomal MicroRNA-223

(Non-Patent Document 5) Non-Patent Document 5: TRADITIONAL CHINESE MEDICINE AND NEURAL REGENERATION Year: 2013|Volume: 8|Issue: 18|Page: 1637-1643 Paeonol attenuates inflammation-mediated neurotoxicity and microglial activation (Non-Patent Document 6) Non-Patent Document 6: Frontiers in Physiology March 2017, Volume 8 Article 193 Prevention of Bleomycin-induced Pulmonary Inflammation and Fibrosis in Mice by Paeonol (Non-Patent Document 7) Non-Patent Document 7: MOLECULAR MEDICINE REPORTS 19: 3217-3229, 2019 Paeonol inhibits the development of 1_chloro_2, 4_dinitrobenzene_induced atopic dermatitis via mast and T cells in BALB/c mice (Non-Patent Document 8) Non-Patent Document 8: Oncotarget 2017; 8:27093-27104 Paeonol suppresses solar ultraviolet-induced skin inflammation by targeting T-LAK cell-originated protein kinase

SUMMARY

The present disclosure provides a novel pharmaceutical composition that effectively treats inflammation while showing excellent effects on the suppression of pruritus and pain by recognizing the problem of showing little effect on itching and pain caused by the inflammatory reaction due to the focus only on the treatment of clean wounds in the case of the prior art, such as Madecassol™ or Fucidin™, and in response, addressing the cut treatment ointments of the related art.

The present disclosure also provides a pharmaceutical use of a novel pharmaceutical composition that effectively treats inflammation while showing excellent effects in suppressing pruritus and pain.

The present disclosure also provides a method of easily manufacturing a novel pharmaceutical composition having such excellent functionalities described above.

In addition, the present disclosure is not limited to these technical problems, and furthermore, the present disclosure also provides other objectives that can be easily derived by those skilled in the art from the general description of the present specification in addition to the objectives described above.

The purpose of the present disclosure is to provide ointments of a new combination of paeonol with other specific pharmaceutical compositions, based on the fact that paeonol is known to be effective in relieving local pain due to its anti-inflammatory effect, which is identified through many animal experiments, in which the ointments are very effective in relieving itching and pain during treatment along with the treatment of clean wounds.

According to one or more embodiments, a composition for external application includes, as an active ingredient, paeonol and panthenol.

The term "paeonol" used herein includes derivatives thereof and pharmaceutically acceptable salts thereof, and likewise, the term "panthenol" used herein includes derivatives thereof and pharmaceutically acceptable salts thereof.

Accordingly, the composition for external application of the present disclosure may include one or more selected from paeonol, derivatives thereof, and pharmaceutically acceptable salts thereof, and one or more selected from panthenol, derivatives thereof, and pharmaceutically acceptable salts thereof.

In an embodiment of the present disclosure, the composition for external application may include paeonol in an amount of 0.1% (w/w) to 3% (w/w), 0.5% (w/w) to 2% (w/w), or 1% (w/w) to 2% (w/w), based on the total weight of the composition for external application.

In an embodiment of the present disclosure, the composition for external application may include panthenol in an amount of 0.5% (w/w) to 6% (w/w), 2% (w/w) to 5% (w/w), or 4% (w/w) to 5% (w/w), based on the total weight of the composition for external application.

In an embodiment of the present disclosure, the composition for external application may further include at least one selected from *Centella asiatica*, coenzyme Q10, neomycin sulfate, and pharmaceutically acceptable salts of these, in an amount of 4% (w/w) to 7% (w/w), or 5% (w/w) to 6% (w/w) based on the total weight of the composition for external application.

In some embodiments, based on the total weight of the composition for external application, the amount of *Centella asiatica* may be from 0.5% (w/w) to 1.5% (w/w), or 1% (w/w), the amount of Q10 may be from 0.5% (w/w) to 1.5% (w/w), or 1% (w/w), and the amount of neomycin sulfate may be from 3% (w/w) to 4% (w/w), or 3.5% (w/w).

The composition for external application of the present disclosure may be provided for treatment of a wound, inflammation inhibition, pruritus reduction, and/or pain relief.

In an embodiment of the present disclosure, the wound may be abrasions, scrapes, incisions, lacerations, skin punctures, tears, bruises, scars or blisters, or wounds associated with any of these.

In an embodiment of the present disclosure, the wound may be a wound causing itching and pain.

On the other hand, the present disclosure provides a method of treating wounds and alleviating pruritus, including applying the composition for external application on skin wounds of a subject.

The present disclosure also provides the use of the composition for external application as described above for the manufacture of a medicament for the treatment of skin wounds and/or alleviation of pruritus.

In relation to the medical ointment of a novel combination containing paeonol and panthenol of the present disclosure configured as described above, specific ingredients that are effective in relieving local pain are combined with ingredients that have other effects in a certain ratio so that the problems of conventional wound healing ointments are addressed to effectively treat inflammation while showing excellent effects in relieving itching and reducing pain. Also, a pharmaceutical use of a medical ointment having such novel combination provides a useful effect to solve the problems required in the above prior art.

DETAILED DESCRIPTION

The ointments of the related art are concentrated only on the treatment of clean wounds, that is, they have limitations in alleviating itching and pain caused by the inflammatory reaction that occurs due to the reasons described above during the treatment process. Therefore, various studies have been conducted to solve this problem. For example, Korea Patent Publication No. 2018-0124424 discloses: *Fusidium coccineum* strain (Accession No.: KCCM12013P) which is isolated from ginkgo leaves, forms pale yellow colonies, and having the ability to increase the expression of any one of Filaggrin, ceramide synthetase 3, b-glucocerebrosidase, and AQP3, and the ability to inhibit the expression of at least one of IL-1a, IL-6, and TSLP; and a composition for improving skin beauty, including the culture as an active ingredient, wherein the improvement of skin beauty is skin barrier strengthening, skin moisturizing, skin cell regeneration, skin vitality increase, being antioxidant, being anti-inflammatory, or being anti-atopic.

However, although the disclosure of Korea Patent Publication No. 2018-0124424 described above may also alleviate pruritus due to the skin moisturizing effect, itching and pain may not be relieved to a satisfactory level at the same time, and thus the solution to this conventional problem is still needed.

The inventors of the present application recognized such problems and studied to address the same, and found that a new combination of medical ointment containing paeonol effectively controls the inflammatory response while retaining the wounds healing effect so that pruritus and pain can be relieved to a satisfactory level at the same time.

Hereinafter, the present disclosure will be described in more detail according to embodiments. However, the scope of the present disclosure is not limited thereto.

In the present specification, the present embodiments are provided such that the disclosure of the present disclosure is complete, and is provided to fully inform those of ordinary skill in the art to which the present disclosure belongs, of the scope of the present disclosure, and the scope of the present disclosure is defined only by the claims. Accordingly, in some embodiments, well-known components, well-known operations, and well-known techniques have not been specifically described to avoid the case in which the present disclosure is interpreted unclearly.

The terms used herein are provided to describe embodiments, and are not intended to limit the present disclosure. In this specification, the singular also includes the plural unless otherwise specified in the phrase. In addition, elements and operations referred to as 'include (or include)' do not exclude the presence or addition of one or more other elements and operations.

Terms used in the claims and specification are defined as set forth below, unless defined otherwise. Also, if any term or symbol used herein is not defined as set forth below, the term and symbol shall have ordinary meaning thereof in the art.

The embodiment of this disclosure includes the use of conventional techniques in organic chemistry, molecular biology (including recombinant techniques), microbiology, cell biology, biochemistry, and immunology which are within the skill of the art.

As used in the present specification and the attached claims, in the context of describing an element, and particularly in the context of claims, the singular and the like should be construed as including the singular and the plural, unless otherwise indicated herein or unless contradicted in terms of the context. Recitation of a range of values herein is merely intended to provide a shorthand method of individually referring to each individual value falling within the range, including the upper and lower limits of the range, unless otherwise indicated herein, and each individual value is incorporated herein as if individually recited herein. All methods described herein can be performed in any suitable order unless otherwise indicated herein or otherwise clearly contradicted by context.

According to an embodiment of the present disclosure, the composition for external application of the present disclosure includes paeonol and panthenol as active ingredients.

Paeonol used in the present disclosure is a major component of Cortex Moutan, and as can be inferred from the contents described in Non-Patent Documents 1 to 8, paeonol has the effect of antibacterial, anti-inflammatory, analgesic, immune system strengthening, anti-sensitivity, etc. As such, studies found that since paeonol inhibits capillary infiltration, edema and inflammation are reduced, and since paeonol has an anti-irritant effect on muscle tissue and skin, paeonol can replace an anti-inflammatory and anti-inflammatory agent used in the skin and oral cavity. Moreover, since paeonol has a unique natural mint flavor, it can suppress bad breath, reduce pain and toothache when brushing teeth, and also suppress gout and pain. Specifically, Non-Patent Document 1 discloses that paeonol relieves inflammation and pain by inhibiting the production of inflammatory cytokines, Non-Patent Document 2 discloses that when paeonol is administered to rats with intestinal inflammations through a system specialized to reach the organs, ulcerative colitis (inflammation) in the intestine is removed, Non-Patent Document 3 discloses that when LPS (bacterial toxicity) is administered to a rat model with chronic lung defects, paeonol relieves inflammation, Non-Patent Document 4 discloses amelioration of the inflammatory response, Non-Patent Document 5 discloses that the toxic alleviation effect in neuro gout indicates that there is a help to reduce neuralgia. Non-Patent Document 6 discloses anti-inflammatory, antioxidant, and anti-fibrotic effects, Non-Patent Document 7 discloses that paeonol relieves atopic skin inflammation, Non-Patent Document 8 discloses the effect in relieving inflammation caused by ultraviolet (UV) light.

In addition, such paeonol can be used as a pharmaceutical preparation for back pain, rheumatism pain, neuralgia, coapi fluriverse, etc., and is the stem and root of Cortex Moutan belonging to the Paeoniaceae family, and is an effective component of traditional oriental medicine. In addition, in modern medicine, paeonol has been proven to have various effects including antibiotics, anti-inflammatory, pain relief, anti-sensitivity alleviation, and all immune systems, and has been widely used in medicine, cosmetics, and chemistry. The results of a study conducted by a research team at Chinese University of Hong Kong on 85 patients published in the 'British Journal of Dermatology' show that Lonicerae flos, Herba menthae, Cortex Moutan, Atractylodes Rhizome, and Phellodendri cortex contributed to the improvement of the quality of life of young patients with symptoms of atopic eczema. The results also showed that 33% of patients taking capsules containing a pharmaceutical extract of the above species had an increase in the quality of life. Additionally, additional studies found that blood levels of four proteins that causes inflammation associated with eczema were reduced in people who took the capsules.

*Centella asiatica*, a component of the present disclosure, exhibits, as a skin regeneration effect, a rapid skin regeneration effect, and an anti-inflammatory effect. Documents show that, in relation to pigmentation in the skin, which is one of skin damage caused of UV light of the sun, *Centella* prevents the pigmentation, reduces traces of cell wounds caused by skin damage, and has the effect of preventing cellulitis, that is, swelling of the connective tissue of the skin (see document 'Postepy Dermatol Alergol 2013 February; 30(1): 46-49 Published online 2013 Feb. 20'), document 'Evidence-Based Complementary and Alternative Medicine Volume 2018, Article ID 9525624' discloses that the *Centella* ingredient cream is effective in actually removing wounds, and document "Evidence-Based Complementary and Alternative Medicine Volume 2012, Article ID848093" discloses that *Centella* ingredient is helpful in the treatment of burns. As described above, it is recognized that *Centella* protects the wound sites from UV to prevent pigmentation after wounding, alleviates uneven bulging of the wound sites, and alleviate traces of wounds, showing excellent skin regeneration ability. Also, it is expected that *Centella* helps burns, abrasions and cut wounds to be regenerated evenly and quickly and helps traces of wounds not to remain.

In addition, according to an embodiment of the present disclosure, pharmaceutically acceptable salts of paeonol and panthenol may be used, and these salts include acid addition salts and base addition salts. Such salts may be prepared by conventional methods, for example, optionally by reaction of the active ingredient with one or more equivalents of an appropriate acid or base in a solvent or medium in which a salt is insoluble, followed by removing the solvent or the medium by using standard techniques. In some embodiments, salts may be prepared by exchanging the counter ion of the active ingredient in the formation of a salt with another counter ion, using a suitable ion exchange resin. Salts include, for example, hydrochloride; bisulfate; maleate; mesylate; tosylate; alkaline earth metal salts, such as a calcium salt and a magnesium salt; or alkali metal salts, such as a sodium salt and a potassium salt.

According to another embodiment of the present disclosure, coenzyme Q10 and neomycin sulfate are each included as a minor ingredient of the ointment of the present disclosure, and the coenzyme Q10 acts to prevent skin damage caused by UV during treatment, is a substance that is a very strong antioxidant and helps the skin, and is actually used a lot as a cosmetic ingredient. Many papers including the following show that coenzyme Q10 helps the prevention of aging and the reduction of winkles, and accordingly, it is expected that coenzyme Q10 helps to regenerate the skin caused by trauma, helps to prevent inflammation in burns, abrasions, cuts, and helps to generate new flesh through an antioxidant function. (Archives of Pharmacal Research June 2009, Volume 32, Issue 6, pp 907-913; MDPI 25 Feb. 2019; Accepted: 13 Apr. 2019; Published: 11 May 2019; and Journal of Aging Research Volume 2018, Article ID 6354680). In addition, panthenol provides the function of preventing itching and drying of the skin. Panthenol is a vitamin B5 component that acts a moisturizing function and is used as a moisturizer in many cosmetic ingredients (J Cosmet Sci, 62, 361-369 (July/August 2011); Am J Clin Dermatol 2002; 3(6):427-33; and Chemistry, Medicine Published in Journal of cosmetic science 2011).

Neomycin sulfate is an antibiotic that is already widely used as an antibacterial agent for skin ointments, and plays an essential role in preventing infection in wound sites.

According to an embodiment of the present disclosure, at least one paeonol or a derivative thereof, for example, a pharmaceutically acceptable derivative thereof, which is a major ingredient of the ointment of the present disclosure, may be included in an amount of 8 wt % to 12 wt % of the total ingredients of the ointment, *Centella asiatica* or a pharmaceutically acceptable salt or solvate thereof may be included in an amount of 5 wt % to 10 wt % of the total ingredients of the ointment, and coenzyme Q10, panthenol, and neomycin sulfate, which are minor ingredients, may be included in an amount of 1 wt % to 2 wt %, 1 wt % to 5 wt %, or 3 wt % to 4 wt % of the total ingredients of the ointment.

In an embodiment of the present disclosure, the ointment may include, based on 1 g of the ointment, 10 mg of paeonol, 5 mg to 10 mg of *Centella asiatica*, 1 mg to 2 mg of coenzyme Q10, 1 mg to 5 mg of paeonol, and 3.5 mg of neomycin sulfate.

The pharmaceutical ointment composition according to the present disclosure is useful in the treatment of inflammation, and the treatment of inflammation includes, irrespective of the cause, the treatment of inflammation on mucosal surfaces of all organs in the body, for example, soft tissues, joints, nerves, vascular systems, internal organs, and the skin.

More specifically, the pharmaceutical ointment composition according to the present disclosure may be used for: the treatment of inflammation caused by wounds, for example, wounds by scrapes, incisions including surgical incisions, lacerations, piercings, tears, bruises and scars, burns, or surgeries resulting from burns, such as skin grafts; and the treatment of other conditions such as hemorrhoids and the like. Wounds of the skin or mucous membrane may result from internal or external physical damage to the membrane surface. Physical wounds may be caused by sharp objects (cuts, incisions, piercings) or dull objects/mechanical forces (lacerations, abrasions, tears), physical blows (bruises), heat or chemicals (burns and blisters), ultraviolet rays (sunburn), or cold (chilblain or frostbite). The wounds may be superficial (damaging only the epidermis and/or dermis) or full-thickness wounds. In severe cases, subcutaneous and/or submucosal tissues, such as muscles, bones, joints and even internal organs, may be damaged.

Scar is the result of inflammation and/or wound healing, and a general term for the formation of fibrous tissue, which is the result of such inflammation/healing. The ointment composition according to the present disclosure may also be useful for inhibiting the production of melanin pigmentation resulting from inflammation or wound healing. The ointment composition of the present disclosure is also useful for the inhibition of: melanin pigmentation, such as melasma, freckles, or melanoma, rashes and other pigmentation of the cheeks, pigmentation caused by melanoma skin cancer, and pigmentation caused by sun exposure; or disorders associated with skin diseases such as acne. Wounds may also occur as a result of a disease or disorder. These may include substances or ulcers of the skin and mucous membranes.

In addition, in relation to the treatment of wounds caused by burns, abrasions, and cuts as described above, the treatment is completed such that new flesh sprouts are generated rapidly without infections and any trace of wounds. The pharmaceutical ointment composition according to the present invention is to provide these effects.

Traces of wounds are usually caused by results, occurring when the skin is regenerated, due to skin damage caused by secondary infection resulting from inflammation and sun exposure, for example, exposure to UV, and skin irritation caused by decreased moisturizing ability, during the treatment. The ointment composition of the new combination of the present disclosure, based on helping the rapid regeneration of wounds, reduces inflammation, prevents oxidation caused by UV, and provides a moisturizing effect, so that, when the skin is damaged, the wound is treated such that the skin is recovered to be the closest to the original skin thereof without any trace of wounds, while alleviating itching and suppressing pain during treatment.

Additionally, in the context of this disclosure, the term "treatment" includes a therapeutic or temporary regimen, the treatment of a patient in need thereof, the prophylactic treatment, and the diagnosis of a patient susceptible to an inflammation or an inflammatory disorder, and the term "patient" includes mammalian (especially human) patients.

Suitable pharmaceutical formulations are commercially available, or otherwise prepared according to the techniques described in documents, for example, the document 'Remington The Science and Practice of Pharmacy, 22nd edition, Pharmaceutical Press (2012) and Martindale—The Complete Drug Reference, 38th Edition, Pharmaceutical Press (2014)' and other documents cited in this document, and the relevant disclosures of all of these documents are incorporated herein by reference. In addition, the preparation of suitable formulations including paeonol, or derivatives and salts thereof, and, in particular, combined formulations used in this disclosure, may be accomplished in a non-disclosure manner by a person skilled in the art by using general techniques.

The active ingredient of an ointment according to the present disclosure may additionally be combined with suitable excipients to prepare the followings: gel formulations (gel matrix materials suitable for this purpose include cellulose derivatives, carbomers and alginates, gummi tragacanthae, gelatin, pectin, carrageenan, gellan gum, starch, xanthan gum, cationic guar gum, agar, non-cellulosic polysaccharides, vinyl polymers, acrylic resins, polyvinyl alcohol, carboxyvinyl polymers and, in particular, hyaluronic acid); lotions (condensates; matrix materials suitable for this purpose include cellulose derivatives, glycerin, non-cellulosic polysaccharides, polyethylene glycols of different molecular weights, and propanediol); pastes or ointments (suitable paste matrix materials for this purpose include glycerin, vaseline, paraffin, polyethylene glycols of different molecular weights, etc.); and creams or foams (suitable excipients for this purpose (for example, forming agents) are hydroxypropyl methyl cellulose, gelatin, polyethylene glycols of different molecular weights, sodium dodecyl sulfate, sodium fatty alcohol polyoxyethylene ether sulfonate, corn gluten powder, and acrylamide).

In addition, while vaseline may be used for use in applying such dressings to wounds, the compositions of the present disclosure may also be combined with a matrix material to make a dressing without the need for the ointment of the present disclosure to use vaseline.

The present disclosure may be subjected to various transformations and may have various embodiments. The following specific embodiments are illustrated in the drawings and described in detail in the detailed description. However, the present disclosure is not intended to limit specific embodiments, and it should be understood to include all transformations, equivalents, or substitutes included in the concept and scope of the present disclosure. In describing the present disclosure, if it is determined that a detailed description of a related known technology may make the gist of the present disclosure unclear, a detailed description thereof will be omitted.

PREPARATION EXAMPLE

Preparation Example 1. Preparation of Ointments According to the Amount of Paeonol Ointments prepared by varying the amount of paeonol were prepared with the ingredients and composition ratios of Table 1 below.

TABLE 1

| | | | Experimental group | | | | | |
|---|---|---|---|---|---|---|---|---|
| No. | Material name | Amount | Not-treated group | Control | Sample 1 | Sample 2 | Sample 3 | Control Madecassol |
| 1 | Paeonol | % | − | − | 0.2% | 0.5% | 1% | |
| 2 | *Centella asiatica* | 1% | − | − | + | + | + | |
| 3 | Coenzyme Q10 | 1% | − | − | + | + | + | |
| 4 | Panthenol | 2% | − | − | + | + | + | |
| 5 | Neomycin sulfate | 3.5 mg/g | − | − | + | + | + | |
| 6 | Cetyl alcohol | 70 mg/g | − | + | + | + | + | |
| 7 | Liquid paraffin | 150 mg/g | − | + | + | + | + | |
| 8 | Glycerin | 10 mg/g | − | + | + | + | + | |
| 9 | Propylene glycol | 80 mg/g | − | + | + | + | + | |
| 10 | Sorbitan Stearate | 30 mg/g | − | + | + | + | + | |
| 11 | Polysorbate 60 | 40 mg/g | − | + | + | + | + | |
| 12 | 1,2-Hexanediol | 2% | − | + | + | + | + | |
| 13 | Purified water | Appropriate amount | − | + | + | + | + | |

Preparation Example 2. Preparation of Ointments According to the Amount of Panthenol Ointments prepared by varying the amount of panthenol were prepared with the ingredients and composition ratios of Table 2 below.

TABLE 2

| | | | Experimental group | | | | | |
|---|---|---|---|---|---|---|---|---|
| No. | Material name | Amount | Not-treated group | Control | Sample 4 | Sample 5 | Sample 6 | Control Madecassol |
| 1 | Paeonol | 0.5% | − | − | + | + | + | |
| 2 | *Centella asiatica* | 1% | − | − | + | + | + | |
| 3 | Coenzyme Q10 | 1% | − | − | + | + | + | |
| 4 | Panthenol | % | − | − | 1% | 2% | 4% | |
| 5 | Neomycin sulfate | 3.5 mg/g | − | − | + | + | + | |
| 6 | Cetyl alcohol | 70 mg/g | − | + | + | + | + | |
| 7 | Liquid paraffin | 150 mg/g | − | + | + | + | + | |
| 8 | Glycerin | 10 mg/g | − | + | + | + | + | |
| 9 | Propylene glycol | 80 mg/g | − | + | + | + | + | |
| 10 | Sorbitan Stearate | 30 mg/g | − | + | + | + | + | |
| 11 | Polysorbate 60 | 40 mg/g | − | + | + | + | + | |
| 12 | 1,2-Hexanediol | 2% | − | + | + | + | + | |
| 13 | Purified water | Appropriate amount | − | + | + | + | + | |

EXPERIMENTAL EXAMPLES

1. Confirmation of the Wound Treatment Effect

The hair of the 6-week aged rat was removed and a wound with a diameter of 8 mm was made therein by using biopsy punches. Then, the rat was treated with the ointments prepared according to Preparation Examples 1 and 2, and on the third day, the image of the wound site was obtained, and the size of the wound site was measured by using a ruler. Three days after the measurement, the size of the wound site was measured.

Figure 1A:
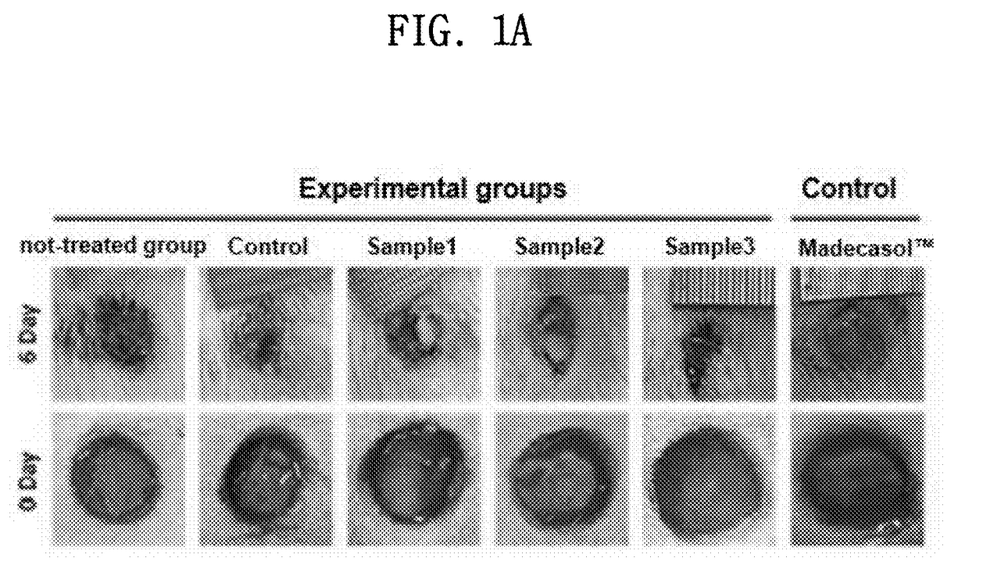
FIG. 1A and FIG. 1B show images of wounds, showing the treatment effect of samples 1 to 3 prepared by varying the amount of panthenol 2% and paeonol.
Figure 1B:
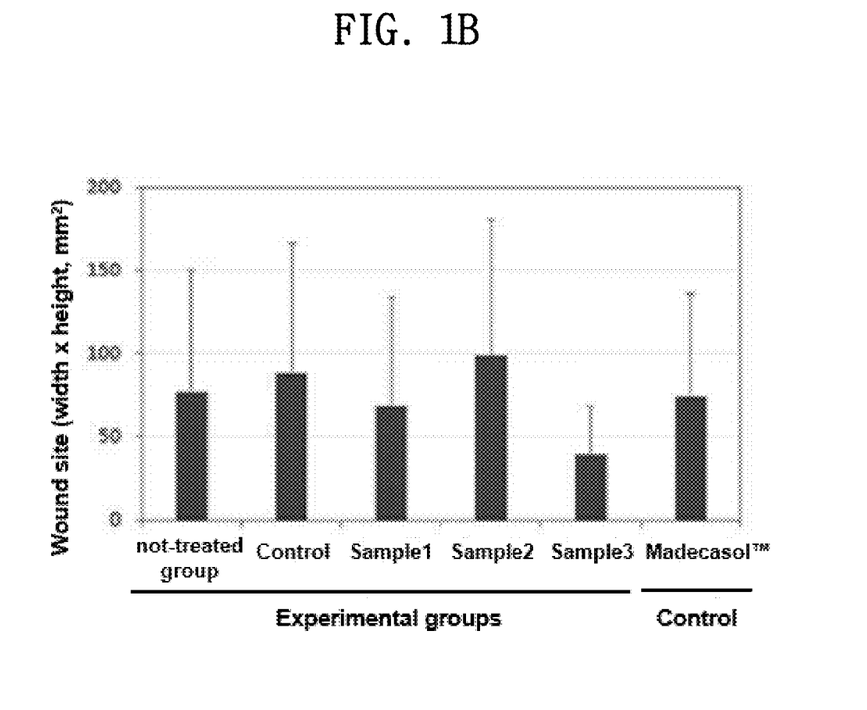
Figure 2A:
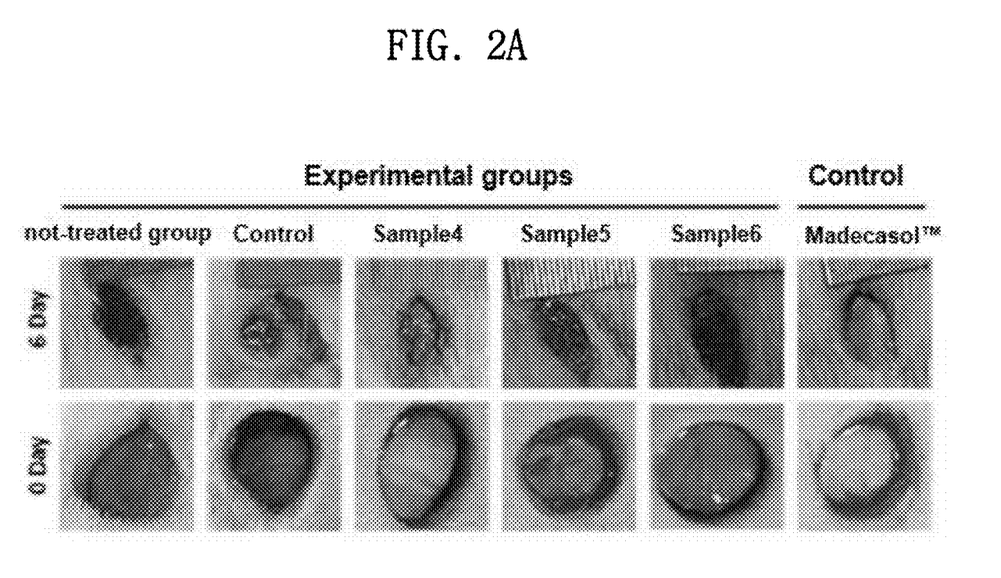
FIG. 2A and FIG. 2B show images of wounds, showing the treatment effect of samples 4 to 6 prepared by varying the amount of panthenol 0.5% and paeonol.
Figure 2B:
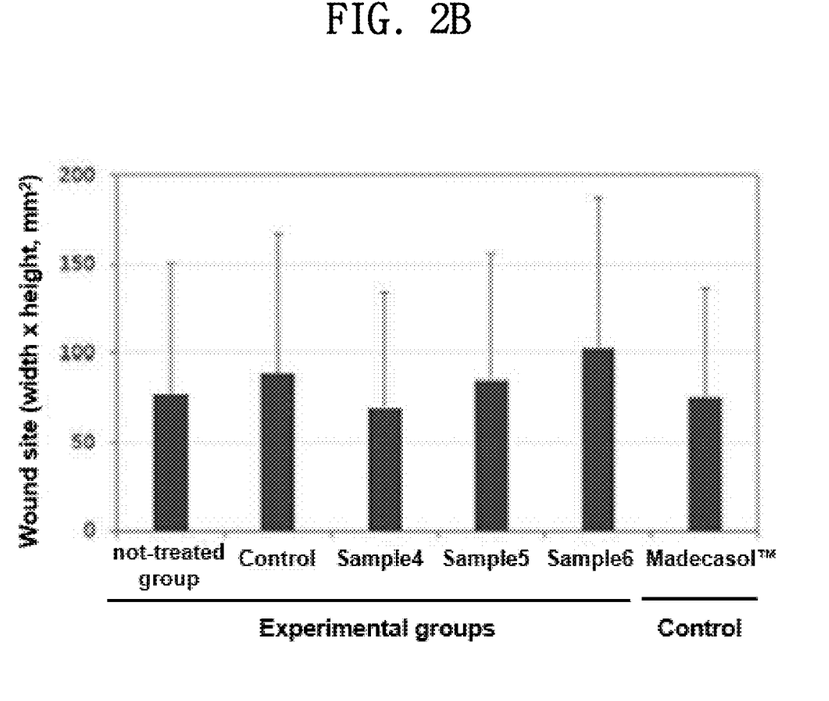

As a result, from among Samples 1 to 3 including different amounts of paeonol, Samples 1 and 2 had no significant difference compared to the control group, and the ointment (Sample 3) including 1% (w/w) of paeonol had higher wounds treatment effect than the control group. (FIG. 1A and FIG. 1B). On the other hand, Samples 4 to 6 with different amounts of panthenol did not show a significant difference compared to the control group in terms of the heating of wounds (FIG. 2A and FIG. 2B).

2. Confirmation of Itching Alleviation Effect

The rats of Example 1 having induced wounds were treated with the ointments prepared according to Preparation Examples 1 and 2, and, once every 3 days, the behavior of touching or scratching the wounds sites for 10 minutes was identified to evaluate the degree of itching.

Figure 3A:
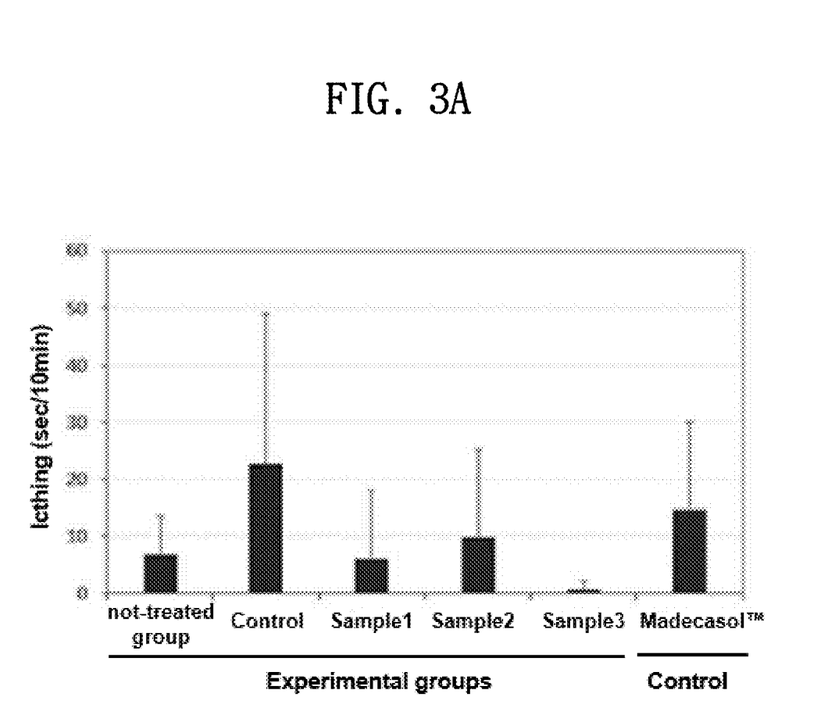
FIG. 3A and FIG. 3B show images of wounds, showing the itching relief effect of samples 1 to 6 prepared by varying the amount of panthenol and paeonol.
Figure 3B:
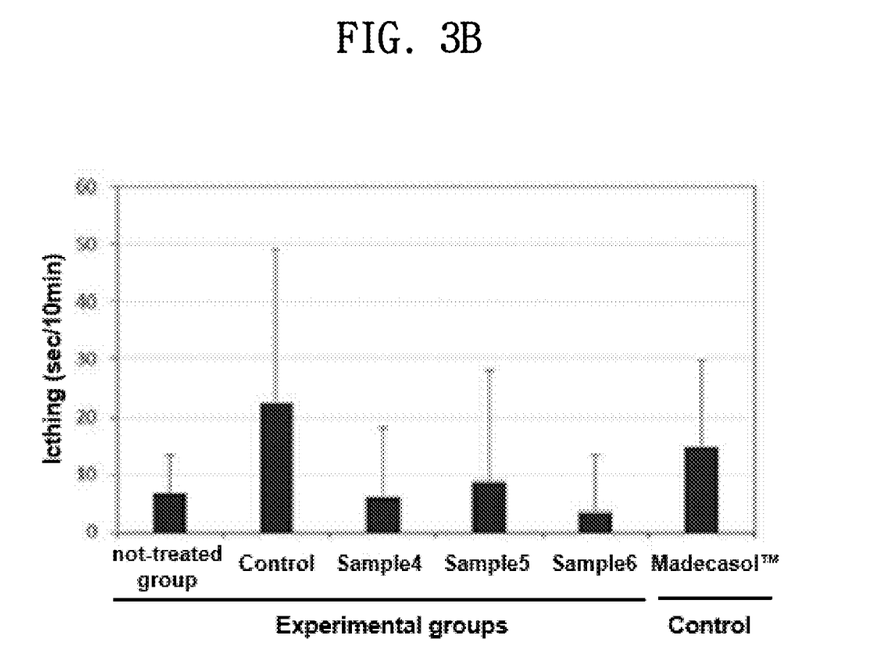

As a result, it can be seen that Samples 1 to 6 prepared by varying the amount of paeonol or panthenol all showed the excellent effect in alleviating pruritus compared to the control group, and, in particular, the pruritus alleviation effect of Samples 3 and 6 were excellent (FIG. 3A and FIG. 3B).

As described above, although the technical concept of the present disclosure has been specifically described in embodiments, it should be noted that the embodiments are provided herein for illustrative purpose only and are not intended to limit the present disclosure. It is obvious to those skilled in the art that various variations and modifications can be made within the scope of the technical concept of the present disclosure, and therefore, it is natural that such variations and modifications belong to the attached claims.

What is claimed is:

1. A method of relieving or reducing wound, inhibiting inflammation or reducing pruritus, comprising applying to a subject in need thereof a composition for external application comprising 0.1% (w/w) to 3% (w/w) paeonol, 0.5% (w/w) to 6% (w/w) panthenol, 0.5% (w/w) to 1.5% (w/w) *Centella asiatica,* 0.5% (w/w) to 1.5% (w/w) coenzyme Q10 and 3% (w/w) to 4% (w/w) neomycin sulfate as active ingredients, based on the total weight of the composition.

2. The method of claim 1, wherein the wound is an abrasions, scrapes, incisions, lacerations, skin punctures, tears, bruises, scars or blisters, or wounds associated with any of these.

3. The method of claim 1, wherein the wound is a wound that causes itching and pain.

\* \* \* \* \*